United States Patent [19]
Lewis et al.

[11] Patent Number: 6,146,325
[45] Date of Patent: Nov. 14, 2000

[54] VENTRICULAR ASSIST DEVICE

[75] Inventors: Jeffrey P. Lewis, Wyomissing; Troy A. Werley, West Lawn; Raymond Newswanger, Terre Hill; Glenn Fulmer, Oley, all of Pa.

[73] Assignee: Arrow International, Inc., Reading, Pa.

[21] Appl. No.: 09/325,334

[22] Filed: Jun. 3, 1999

[51] Int. Cl.⁷ .................................................. A61M 1/12
[52] U.S. Cl. ................................................. 600/16; 623/3
[58] Field of Search ........................... 600/16–18; 923/3, 923/12, 14, 24, 25; 604/48, 52, 53, 65–67, 151, 153

[56] References Cited

U.S. PATENT DOCUMENTS

| | | |
|---|---|---|
| 4,105,016 | 8/1978 | Donovan, Jr. . |
| 4,397,049 | 8/1983 | Robinson et al. . |
| 4,427,470 | 1/1984 | Kolff . |
| 4,512,726 | 4/1985 | Strimling . |
| 4,547,911 | 10/1985 | Strimling . |
| 4,820,300 | 4/1989 | Pierce et al. . |
| 4,820,301 | 4/1989 | Chareire et al. . |
| 4,888,011 | 12/1989 | Kung et al. . |
| 4,981,484 | 1/1991 | Holfert et al. ............................... 623/3 |
| 4,994,078 | 2/1991 | Jarvik . |
| 5,041,131 | 8/1991 | Nagase . |
| 5,041,132 | 8/1991 | Miyata . |
| 5,135,539 | 8/1992 | Carpentier . |
| 5,222,980 | 6/1993 | Gealow . |
| 5,267,940 | 12/1993 | Moulder . |
| 5,282,849 | 2/1994 | Kolff et al. . |
| 5,314,469 | 5/1994 | Gao ............................................... 923/3 |
| 5,332,403 | 7/1994 | Kolff . |
| 5,417,663 | 5/1995 | Slettenmark . |
| 5,456,715 | 10/1995 | Liotta . |
| 5,599,173 | 2/1997 | Chen et al. . |
| 5,688,245 | 11/1997 | Runge . |
| 5,713,954 | 2/1998 | Rosenberg et al. . |
| 6,001,056 | 12/1999 | Jassawalla et al. ........................ 600/16 |
| 6,066,085 | 5/2000 | Heilman et al. ........................... 600/16 |

*Primary Examiner*—Jeffrey R. Jastrzab
*Attorney, Agent, or Firm*—Amster, Rothstein & Ebenstein

[57] ABSTRACT

An implantable VAD (preferably an LVAD) includes a compliance chamber which forms a reservoir for liquid extending from adjacent the bottom of the compliance chamber upwardly towards the top of the compliance chamber, and a chamber for gas disposed above the liquid reservoir and extending upwardly to the top of the compliance chamber. The gas chamber is in gaseous communication with a blood pump via a conduit. A subcutaneous port is in liquid and gaseous communication with the liquid reservoir via a second conduit for introducing make-up gas into or removing excess gas from the gas chamber via the liquid reservoir and for removing accumulated liquid from the liquid reservoir. An outlet cannula comprises a hard polymer tubing commencing adjacent the pump and a relatively soft graft tubing terminating adjacent the tube adapted to enter the aorta, a distal end of the hard polymer tubing and a proximal end of the graft tubing being secured together by a snap-fit connector. A sewable apical cuff is provided for sewing attachment of the inlet cannula to a chamber of the heart, and a collet ring clamp secures together the distal end of the apical cuff and the distal end of the tube.

17 Claims, 8 Drawing Sheets

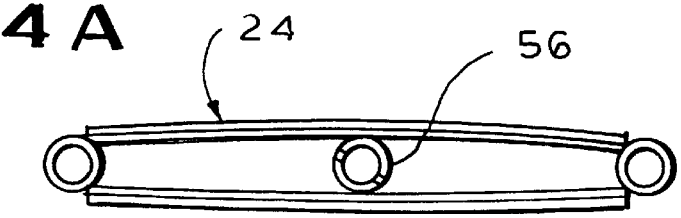
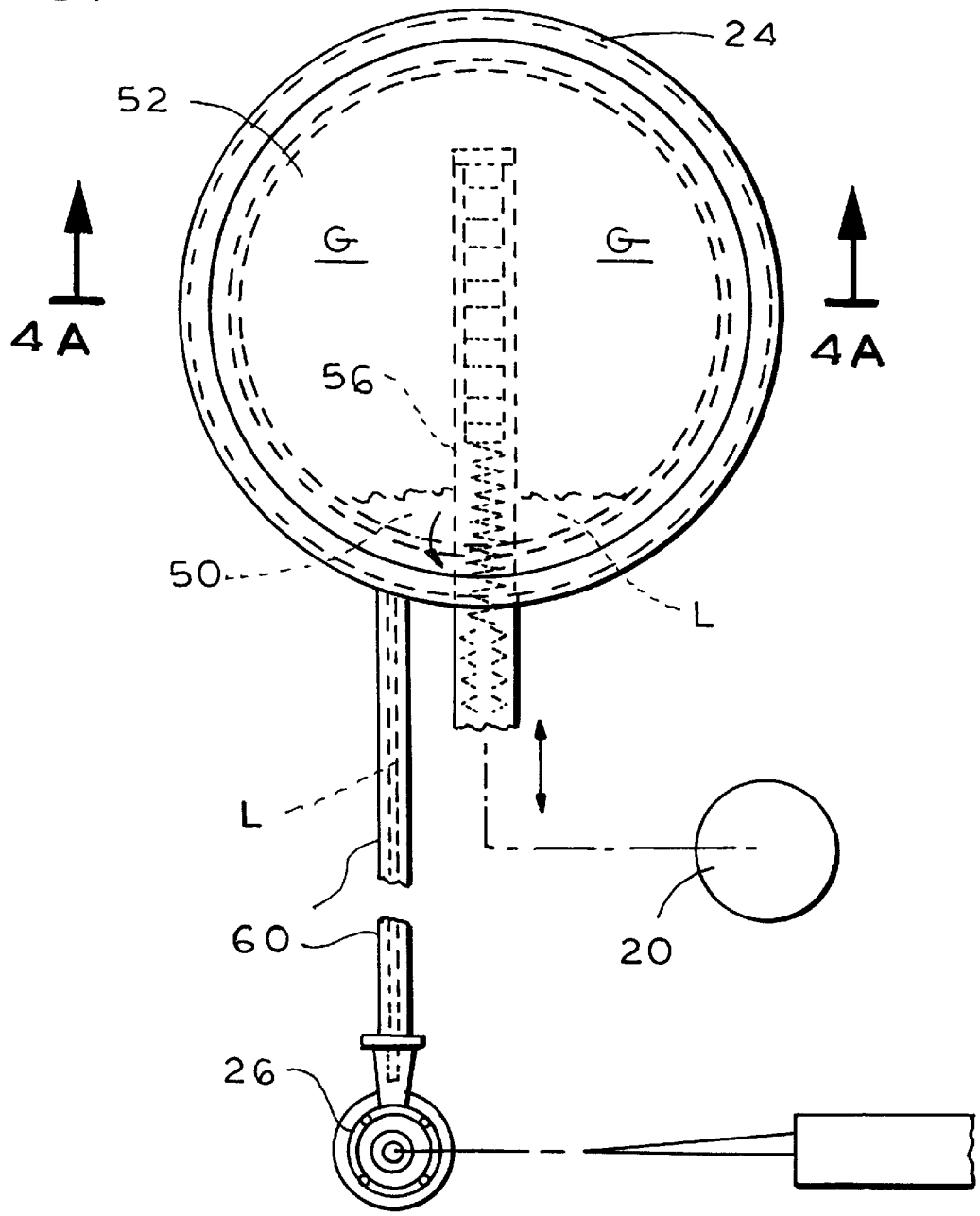

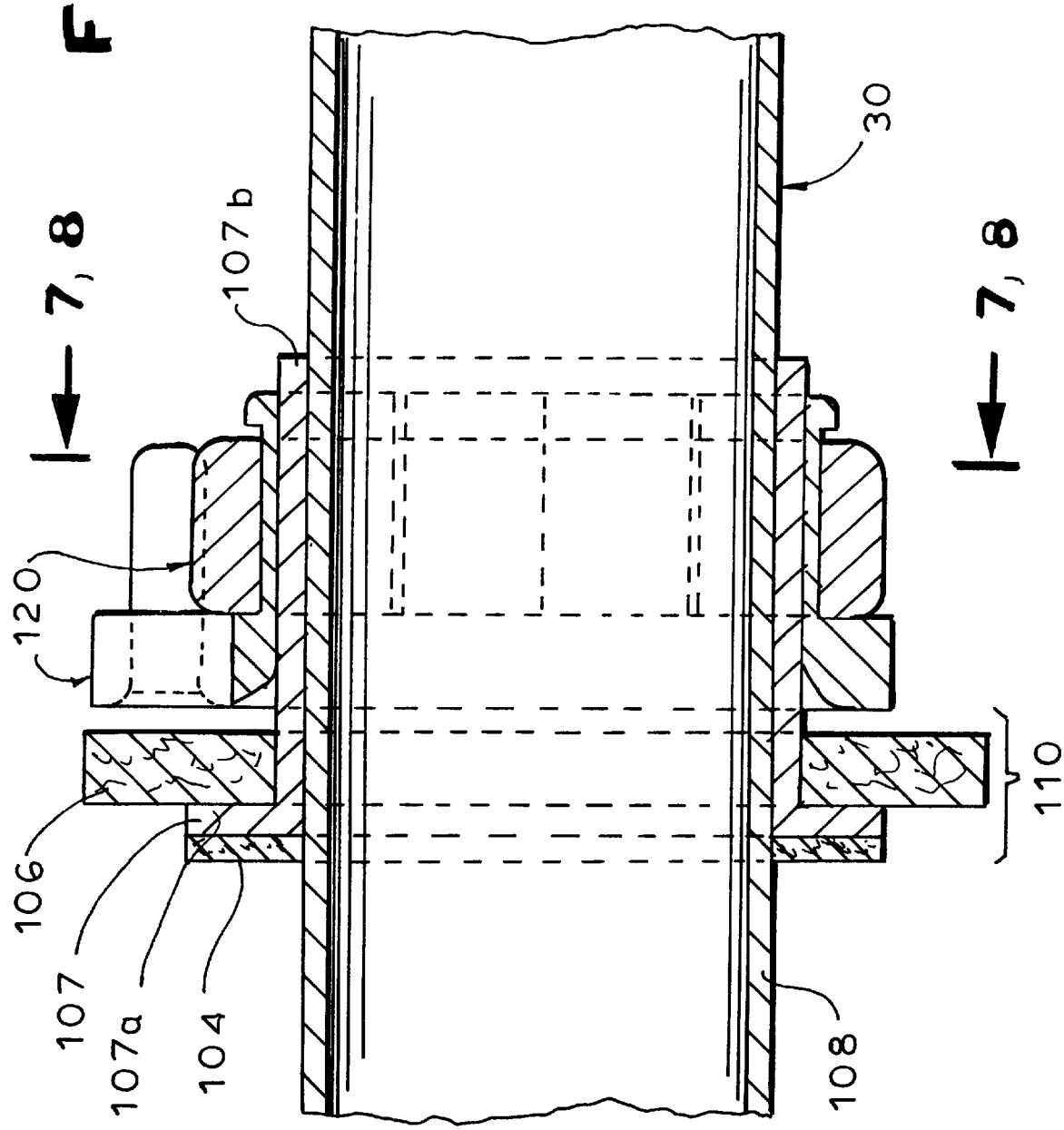

VENTRICULAR ASSIST DEVICE

BACKGROUND OF THE INVENTION

The present invention relates to a ventricular assist device (VAD), and more particularly to a VAD which is essentially implantable in a patient.

VAD's and LVAD's, and especially VAD's and LVAD's which are more or less implantable within the body of a patient, are well known in the art. The LVAD was developed for the treatment of end stage congestive heart failure (CHF) in patients who are on maximal medical therapy and require long-term mechanical circulatory support, for example, patients who are not (temporarily or permanently) candidates for heart transplantation. Accordingly, the LVAD replaces or augments the function of the left ventricle in patients whose native left ventricles are unable to supply sufficient cardiac output to support a reasonable lifestyle, but whose right ventricle does function acceptably. The primary purpose of the LVAD, therefore, is to provide systemic blood flow equal to that provided to it by the right heart. Secondarily, it should do so in a manner that drains the pulmonary veins and left atrium effectively, thereby avoiding pulmonary complications that would affect pulmonary or right heart function.

Alternatively a VAD could be applied to replace or augment the function of the right ventricle. For the purposes of the present invention the VAD design applies to both LVAD's and RVAD's.

The implantable subsystems of the LVAD include: inlet and outlet cannulae, blood pump, controller, internal coil, compliance chamber, and infusion port subsystems. The external or non-implantable subsystems of the LVAD include: power transmitter (PT) with external coil, power pack, and battery charger. The implantable and external subsystems work together to supplement the depressed cardiac-output state of a patient whose heart is failing.

However, the known more-or-less implantable LVAD's have not proved to be entirely satisfactory in use for a variety of different reasons as follows:

First, the gas passing between the blood pump and the compliance chamber typically carries with it entrained or dissolved liquid, such as moisture. This entrained or dissolved liquid separates from the gas within the compliance chamber due to the temperature differential between the substantially spaced apart pump and compliance chamber, and under the influence of gravity accumulates at the bottom of the compliance chamber. The collected liquid at the bottom of the compliance chamber consumes its volumetric space and reduces the functionality of the chamber, thereby decreasing the efficiency of the pump.

Second, the outlet cannula is connected to the blood pump at one end and to the aorta at the other end. If the outlet cannula is formed exclusively of polymer tubing, the anastomotic connection between the tube and the patient's aorta would be difficult. If the outlet cannula is formed exclusively of hard polymer tubing, then the outlet cannula is too rigid and lacks the flexibility to accommodate various movements of the patient during use. Accordingly, it is common practice to have an outlet cannula which comprises a hard polymer tubing commencing adjacent the pump and a relatively soft woven graft tubing (e.g., made of woven dacron, PTFE, etc.) adjacent to the aorta. Clearly, the securing together of the distal end of the hard polymer tubing and the proximal end of the graft tubing must provide a smooth transition and be easy to effect in manufacturing.

Third, an inlet cannula is connected to the blood pump at a proximal end and to a titanium tube entering a heart chamber (e.g., the left ventricle) at a distal end. Preferably the distal end of the inlet cannula includes a sewable flexible apical cuff to facilitate attachment of the cannula to the heart chamber (e.g., the left ventricle) myocardium via surgical sewing. The means conventionally used for securing together the apical cuff and the titanium tube are complex and unreliable. The securing means must be easily utilized during the surgical implantation procedure and establish a reliable connection thereafter as a failure of the connection would be critical.

Accordingly, it is an object of the present invention to provide an improved VAD and, more particular, an improved implantable VAD.

Another object is to provide a VAD enabling accumulated liquid within the compliance chamber to be withdrawn through a subcutaneous port.

A further object is to provide a VAD including means for easily and reliably securing together in the outlet cannula the hard polymer tubing and the woven graft tubing.

It is an object of the present invention to provide a VAD including an easy-to-operate and reliable means for securing together the apical cuff and the tube entering the heart chamber (e.g., the left ventricle).

It is also an object to provide a VAD which has means for draining accumulated liquid from the compliance chamber through a subcutaneous port, an inlet cannula having components which are easily and reliably secured together without relative rotation thereof, and means for easily and reliably securing together a tube entering the heart chamber (e.g., the left ventricle) and a sewable flexible apical cuff.

It is another object to provide such a VAD which is simple and economical to assemble, implant and maintain.

SUMMARY OF THE INVENTION

It has now been found that the above and related objects of the present invention are obtained in an implantable VAD including a pump, a compliance chamber disposed above the pump, and a cannula connecting the pump and the compliance chamber in liquid and gaseous communication. The compliance chamber forms a reservoir for liquid extending from adjacent the bottom of the compliance chamber upwardly towards the top of the compliance chamber and a chamber for gas disposed above the liquid reservoir and extending upwardly to the top of the compliance chamber, the gas chamber being in gaseous communication with the pump via the cannula. A subcutaneous port is in liquid and gaseous communication with the liquid reservoir for introducing make-up gas into the gas chamber via the liquid reservoir and for removing accumulated liquid from the liquid reservoir. Conduit means connect the port and the liquid reservoir in liquid and gaseous communication.

In a preferred embodiment, a weir disposed in the compliance chamber has one end passing upwardly through the liquid reservoir and in gaseous communication with the gas chamber, and the other end in gaseous communication with the cannula. The conduit means connects the port and the bottom of the liquid reservoir, and the cannula connects the pump and the gas chamber above the top of the liquid reservoir. The top of the liquid reservoir and the bottom of the gas chamber are preferably the same.

The present invention also encompasses an implantable VAD including an outlet cannula connected to a pump at a proximal end and to a tube adapted to enter the aorta at a distal end. The outlet cannula comprises a hard polymer tubing commencing adjacent the pump and a relatively soft, woven graft tubing terminating adjacent the tube. A distal end of the hard polymer tubing and a proximal end of the graft tubing are secured together by a snap-fit connector formed of titanium. Preferably a strain relief material is disposed substantially between portions of the graft tubing and the snap-fit connector, thereby to protect the graft tubing. The strain relief material is preferably formed from a material similar to the hard polymer tubing.

The present invention additionally encompasses an implantable VAD including a sewable flexible apical cuff adapted to be sewn to a portion of the heart (e.g., myocardium) and a rigid tube adapted to enter a chamber of the heart (e.g., the left ventricle). Means for securing together the cuff and tube comprise a collet defining multiple radially compressible, circumferentially curved fingers, and a collar for radially inwardly moving the fingers to crimp a length of the cuff intermediate the collet and the tube onto the tube as the collar is rotated relative to the fingers from an initial relative orientation.

In a preferred embodiment, the outer surface of the fingers defines circumferentially spaced flats and the inner surface of the collar defines circumferentially spaced flats. The fingers and the collar have an initial relative orientation such that the finger flats are radially aligned with the collar flats, and a final relative orientation such that the finger flats and the collar flats are not radially aligned (i.e., are radially offset) such that the inner surface of the collar flats move the finger flats (and hence the fingers) inwardly towards the tube, thereby crimping the apical cuff therebetween. Preferably, in the initial relative orientation the collet is rotatable relative to the tube, and the collar is rotatable relative to the collet.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein:

FIG. 4 is a fragmentary exploded front elevational view, partially in cross-section, of the compliance chamber, subcutaneous port, and conduit means connecting the same;

FIG. 4A is a sectional view taken along the line 4A—4A of FIG. 4;

FIG. 6 is a fragmentary side elevational view, in section, taken along the line 6—6 of FIG. 1 and showing the means for securing together the apical cuff and the tube entering the left ventricle;

DETAILED DESCRIPTION OF THE PREFERRED EMBODIMENTS

Figure 1:
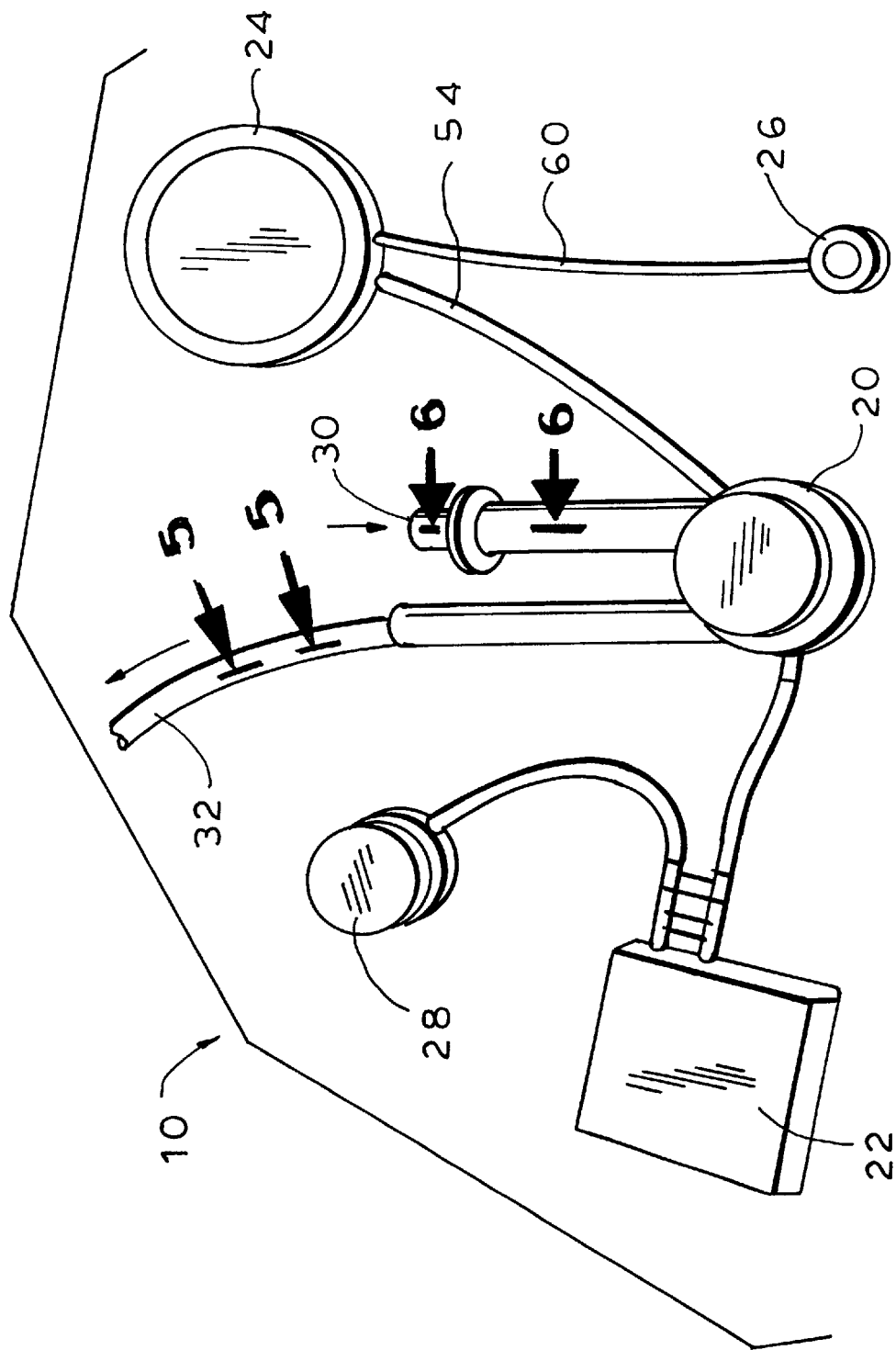
FIG. 1 is an exploded isometric view of the implantable subsystems of the present invention.

Referring now to FIG. 1, therein illustrated are the various implantable subsystems of an LVAD according to the present invention, generally designated by the reference numeral 10, as follows:

A. The blood pump subsystem 20 receives and pumps blood from the heart chamber (e.g., the left ventricle) to the aorta via two cannulae (the below-mentioned inlet and outlet cannulae 30, 32) and one-way valves. It acts in parallel and asynchronously to the heart chamber (e.g., the left ventricle).

B. The controller subsystem 22 receives power via an induction process and rectifies the power for use in controlling the pump motor 20. It transmits and receives telemetry through an enclosure, dispenses power rectified from an external source, charges internal battery power, and transmits data about the internal battery state via an inductive coil path.

C. The compliance chamber 24 and subcutaneous infusion port 26 subsystem compensates for gas volume displacement produced by blood-sac volume changes and gas volume losses due to diffusion through the blood-sac in the blood pump subsystem 20.

D. The internal coil subsystem 28 receives power and broadcasts data about the internal battery state of the controller 22.

E. The inlet cannula subsystem 30 provides a transport path of blood from the heart chamber access point (e.g., the left ventricular apex) to the blood pump subsystem 20.

F. The outlet cannula subsystem 32 provides a transport path of blood from the blood pump subsystem 20 to the ascending aorta.

Figure 2:
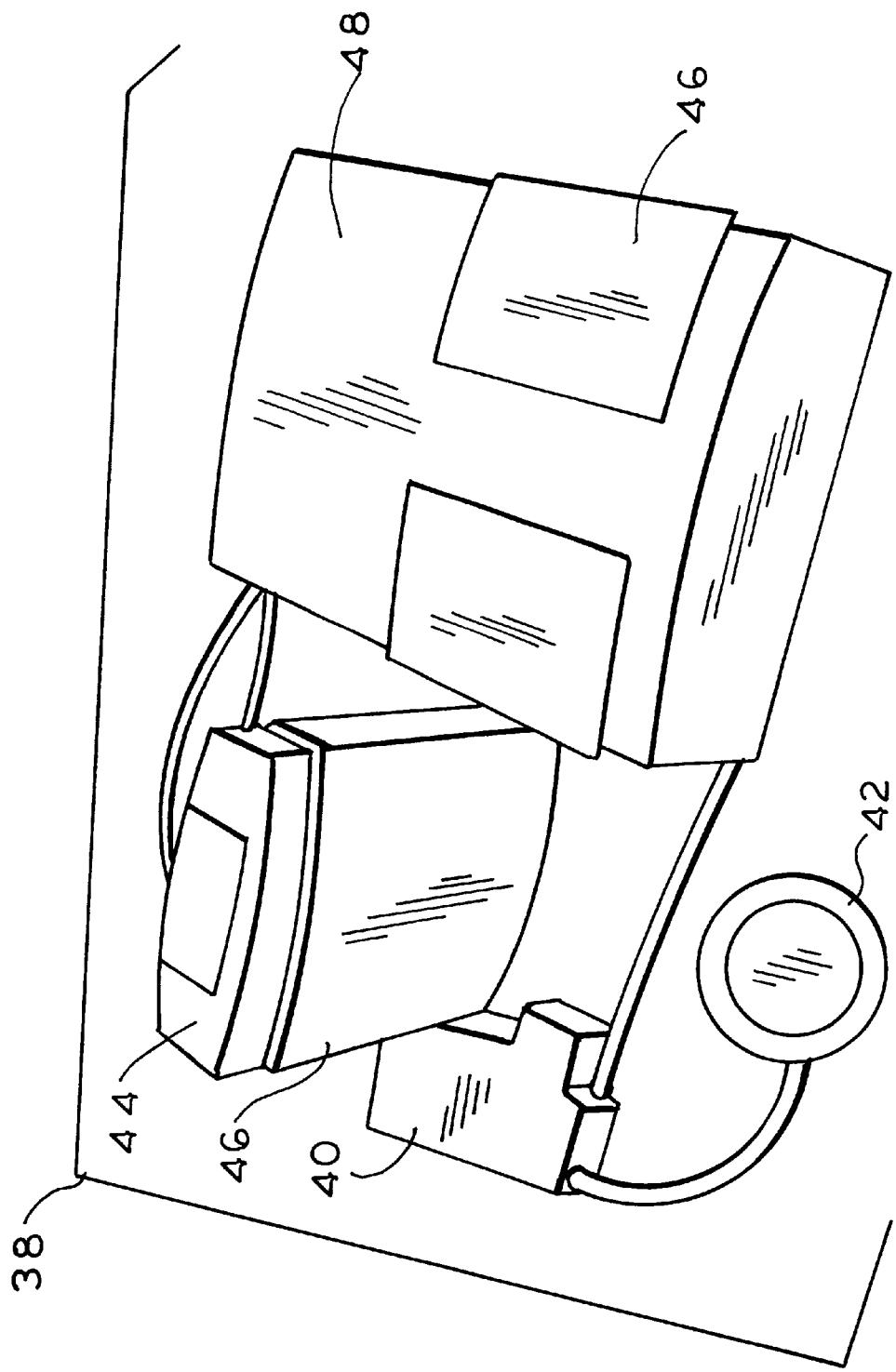
FIG. 2 is an exploded isometric view of the external subsystems of the present invention.

Referring now to FIG. 2, therein illustrated are the various external subsystems (that is, devices maintained outside of the patient's body) which are used in connection with the implantable subsystems as follows:

A. The power transmitter 40 (with external coil 42) subsystem converts the DC power to AC power and transmits the AC power to the implanted controller subsystem 22 via an inductive coil link 42. It also receives data from the controller subsystem 22 about the internal battery state and monitors power performance.

B. The power pack subsystem 44 sends DC power to the power transmitter subsystem 40, using battery packs 46 or an external source, and acts as a performance alarm center. The power pack subsystem 44 may be externally powered either through a lightweight portable power supply which converts AC power to DC power for the power pack, or a lightweight transportation supply which converts DC vehicular power to appropriate DC power for the power pack.

C. The battery charger subsystem 48 charges, refreshes, and tests the removable power pack subsystem batteries 46 on a pass/fail basis.

Additionally, an external system monitor subsystem (not shown) is preferably used to display all broadcast telemetry information from the implanted controller subsystem and to initiate reprogramming of certain implanted controller subsystem settings.

Figure 3:
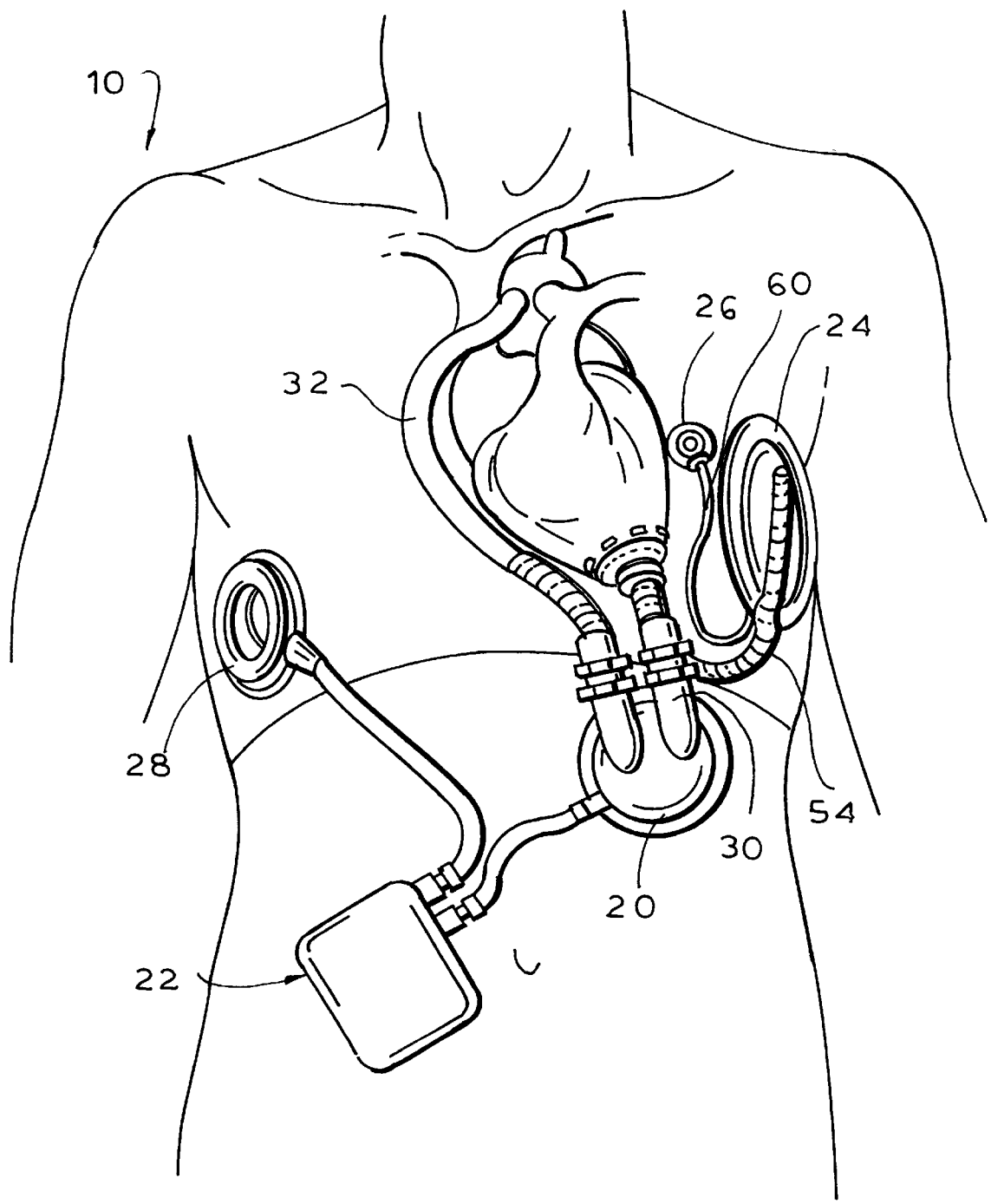
FIG. 3 is a schematic showing general placement of the implantable subsystem within a human body.

Referring now to FIG. 3, therein illustrated is a sketch showing generally, for ease of visualization, the preferred locations of the various implanted LVAD components 10. Clearly, the various components may be relocated from the illustrated sites and still operate according to the principles of the present invention.

More particularly, the external power pack subsystem 44 supplies DC power to the external power transmitter 40, where it is converted to an AC voltage. The external power pack subsystem 44 preferably includes at least a pair of rechargeable batteries 46. The external power transmitter subsystem 40 drives an external ring-shaped external coil 42 that is placed on a patient's skin surface, directly over the implanted internal coil 28. AC power is transmitted through the intact skin from the external coil 42 to the internal coil 28 through induction. From the internal coil 28, power is conducted to the implanted controller 22, where it is rectified to a DC voltage and used to power the implanted controller 22 and to drive the implanted blood pump 20.

The implanted blood pump 20 is a brushless DC motor that drives a pusher-plate in a reciprocating fashion to compress a smooth-walled blood-sac and produce pulsatile flow. The blood-sac has two ports: an inlet and an outlet. One-way, monostrut disk valves control the direction of flow through the ports. During the pump's systole, the pusher-plate compresses the blood-sac and forces blood through the outlet cannula 32 (via the one-way outlet valve), and into the aorta. When the pusher-plate is in the diastole position, the pusher-plate is completely retracted, allowing blood to flow from the heart chamber (e.g., the left-ventricular apex) through the inlet cannula 30 (via the one-way inlet valve), and into the blood-sac.

Compliance or volume compensator chambers are old in the art and are used to provide gas to pump 20 via conduit 54 during the emptying (compression) of the blood-sac or systolic stroke of a pump cycle and to absorb gas from the pump 20 via conduit 54 during the filling of the blood-sac or diastolic stroke of a pump cycle. Thus compliance chamber 24 allows gas to be shuttled to and from the pump 20 as differential pressures are created by the pump's mechanical motion. An implanted infusion port 26 is typically connected, via conduit 60, to the compliance chamber 24 to facilitate gas replenishment when necessary. The gas which enters the compliance chamber 24 from pump 20 (typically air or $CF_6$) may contain dissolved or entrained moisture or gases which condense within the chamber due to a temperature differential and may thereafter flow back to the pump 20, thereby interfering with efficient operation of both the compliance chamber 24 and the pump 20.

The implanted controller 22 contains the electronics necessary to perform the control functions of the implanted blood pump 20. It also contains rechargeable batteries (not shown) as a back-up to the external power supply 44 if the latter were removed from the patient. These rechargeable batteries will supply power to the LVAD for a period of time so that the patient can attend to personal needs for which they choose to be untethered to the external power supply 44. The batteries can rapidly be recharged after the external power supply is coupled once again.

Software algorithms are stored in the implanted controller 22. These algorithms adjust the implanted blood pump's performance contingent upon feedback about the pump's motor position and information about the internal voltage supply of the implanted controller. This feedback provides an inference as to the pump's filling rate, which is in turn an indication of the patient's cardiac output needs. The algorithms will attempt to pump enough blood so that a large percentage of the pump's "blood-sac" is utilized every stroke. The algorithms will manage other tasks such as charging the internal batteries, and providing telemetry communication to the outside world (i.e., an external system monitor).

Another important element of the LVAD system is an external system monitor subsystem. This is used for telemetry communication with the implanted controller and displays all broadcast telemetry information from the controller subsystem and initiates reprogramming of certain controller settings. This monitor is necessary to evaluate the LVAD function in vivo. It can also be used to modify device parameters or download a program change if it is needed.

Biocompatibility requirements include avoidance of hemolysis, thrombosis, or damage to tissues surrounding the device. Control of motor speeds, the manner of implementing cardiac output control, and provisions for limiting power dissipation in the control system, along with aspects of the hardware design, fulfill these requirements.

For reasons of infection control and cosmetics, the system is designed to operate with the patient's skin fully intact.

To the extent possible, device failure should not have sequelae that interfere with remnant native heart function, cause catastrophic loss of blood, or otherwise prevent emergent salvage of the patient. Since successful emergency care of a patient with a non-functioning assist pump and minimal native heart function is seen as possible, device failure should not result in consequential damage (e.g., tissue damage due to overheating) that would prevent or complicate the patient's eventual recovery.

While the LVAD includes both implantable subsystems 10 and external subsystems 38, the entire LVAD is considered to be essentially implantable as the skin is not pierced for connection between the implantable and external subsystems, thus minimizing the chance for infection to pass through the skin.

The implantable LVAD subsystems 10 according to the present invention solve the previously enumerated deficiencies of the known implantable subsystems of an LVAD as described hereinafter.

As aforesaid, the first problem arises because the main stream of gas G passing through the blood pump 20 typically carries with it entrained or dissolved liquids, such as blood or water, and/or condensable gases. This entrained or dissolved liquid and/or condensable gas may separate from the main stream of gas G within the compliance chamber 24 and, under the influence of gravity, accumulate at the bottom of the compliance chamber 24. The collected liquid L at the bottom of the compliance chamber 24 interferes with the proper functioning of the compliance chamber by limiting its contractibility and consuming volumetric space intended for the gas.

Referring now to FIG. 4 in particular, therein illustrated is an assembly of a compliance chamber 24 and a subcutaneous port 26. The compliance chamber 24 forms a reservoir 50 for liquid L extending from adjacent the bottom of the compliance chamber upwardly towards the top of the compliance chamber. The compliance chamber 24 also forms a chamber 52 for gas G disposed above the liquid reservoir 50 and extending upwardly to the top of the compliance chamber. In other words, the gas chamber 52 extends downwardly from the top of the compliance chamber towards the liquid reservoir 50. The gas chamber 52 is in gaseous communication with the implanted blood pump subsystem 20 via a tube 54 connecting the blood pump subsystem 20 and the compliance chamber 24. Thus, the compliance chamber 24 receives the main stream of gas G from, and discharges the main stream of gas G to, the pump 20 via tube 54, the main stream of gas G typically including at least a small amount of entrained or dissolved liquid and/or condensable gas.

It will be appreciated that the tube 54 extends upwardly into the gas chamber 52, well above the liquid reservoir 50. The upper end of the tube 54 directly connects the pump 20 and the gas chamber 52 above the top of the liquid reservoir 50. In other words, in a preferred embodiment the upper end of the tube 54 acts as a weir 56 having one end passing upwardly through the liquid reservoir 50 and in gaseous communication with the gas chamber 52, and the other end in gaseous communication with the pump 20. While the weir 56 is illustrated as being a portion of the tube 54, clearly the weir 56 may be a separate structural element, acting cooperatively with the tube 54, to place the pump 20 and gas chamber 52 in gaseous communication. (It will be appreciated by those skilled in the art that, as used herein, the term "gaseous communication" includes the presence of entrained or dissolved liquid within the gas stream.)

Alternatively, the tube 54 may directly enter the compliance chamber 24 within the gas chamber 52 (that is, without first passing through the liquid reservoir 50), preferably adjacent the top of the gas chamber 52. In this instance, no weir 56 is required.

A conduit 60 has one end extending into the liquid reservoir 50 (preferably at or adjacent the bottom thereof) and the other end secured to the subcutaneous port 26 for liquid and gaseous communication between the liquid reservoir 50 and the port 26. Thus, just as the tube 54 connects the pump 20 and the gas chamber 52 (above the top of the liquid reservoir 50), the conduit 60 connects the port 26 and the bottom (or a level adjacent the bottom) of the liquid reservoir 50.

It will be appreciated that the top of the liquid reservoir 50 and the bottom of the gas chamber 52 are the same and may be disposed at various heights along the longitudinal axis of the compliance chamber 24 so long as the gas G entering and leaving the gas chamber 52 via the weir 56 does so without having to pass directly through the liquid reservoir 50 (that is, the weir 56 protects it from the liquid L in the liquid reservoir 50).

The subcutaneous port 26 is, in certain respects, similar to the conventional "infusion port" used in an LVAD in order to enable air or like gas to be introduced into or removed from the LVAD system to compensate for air or other gas losses or gains through the blood-sac in the blood pump 20. However, unlike the conventional infusion port, the subcutaneous port 26 is used not simply to introduce or remove gas G into or from the implanted LVAD subsystems (and in particular, compliance chamber 24), but also to drain the liquid L from the liquid reservoir 50. Thus, at appropriate levels, the liquid reservoir 50 may be drained entirely of liquid L by a physician using an empty hypodermic needle 59 to establish communication between such needle and the liquid reservoir 50 via the conduit 60. Preferably, the compliance chamber 24 is oriented so that the conduit 60 communicates with the liquid L of the liquid reservoir 50 at the very bottom thereof so as to enable a complete drainage of the reservoir 50 by the physician, although the conduit 60 may alternatively be adjacent the bottom of the liquid reservoir 50 (i.e., slightly off to one side), although this may result in some of the liquid L remaining in the liquid reservoir 50.

During use of the LVAD, the accumulating liquid L in the liquid reservoir 50 may or may not be allowed to enter the conduit 60. The liquid L will tend to enter the conduit 60 and eventually fill it, so long as the height of the liquid L is above the distal end of the conduit 60. On the other hand, if desired, the conduit 60 may be designed so that the column of air trapped within the second conduit 60 resists entry of the liquid L into conduit 60 until the septum of infusion port 26 is penetrated by a physician's hypodermic needle 59 and the column of air aspirated.

Thus the compliance chamber 24/subcutaneous port 26 subassembly of the present invention enables the physician to first substantially drain the liquid L in liquid reservoir 50 from the compliance chamber 24. At this point, the conduit 60 communicates directly with the gas chamber 52 and can be used to introduce make-up or remove excess gas as necessary, without having the gas pass directly through the liquid reservoir 50 in intimate contact with any liquid L therein. Accordingly, the make-up gas introduced into compliance chamber 24 according to the present invention is dry relative to the make-up gas introduced by a conventional infusion port through the accumulated liquid.

Preferably, the end of the tube 54 (or weir 56) extending into the gas chamber 52 contains a plurality of apertures along its circumferential surface within gas chamber 52 so that gas G may be introduced from the tube 54 directly into the gas chamber 52 of the compliance chamber 24 faster than would be the case if the tube 54 (or weir 56) had only a single opening at the tip thereof. Of course, the placement of such side apertures must always be such that the liquid L of liquid reservoir 50 cannot enter therethrough.

The present invention further addresses the second problem noted with the implantable components of LVAD's, namely, the difficulty in securing together in an outlet cannula, the hard polymer tubing (adjacent pump 20) and the graft tubing (adjacent the aorta).

Figure 5:
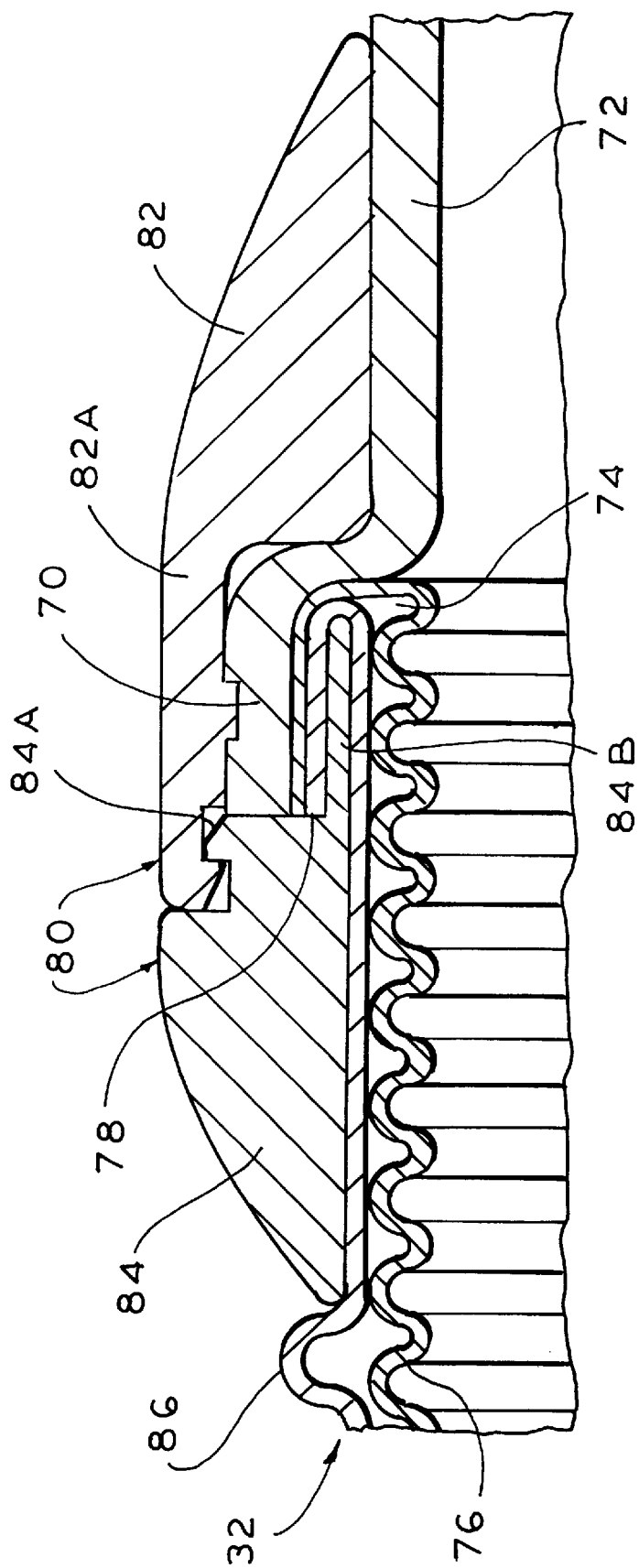
FIG. 5 is a fragmentary side elevational view, in section, taken along the line 5—5 of FIG. 1 and showing the connection of the hard polymer tubing and the graft tubing to form the outlet cannula, with portions thereof being removed to reveal details of internal construction.

Referring now to FIG. 5 in particular, therein illustrated is an outlet cannula 30 according to the present invention. The distal end 70 of the hard polymer tubing 72 and the proximal end 74 of the graft tubing 76 are secured together by a snap-fit connector, generally designated 80, formed of two connector components 82, 84.

The proximal connector component 82 is secured or bonded to the distal end 70 of the hard polymer tubing 72, extends circumferentially thereabout, and is at least strongly resiliently flexible. While the proximal component 82 is secured to the hard polymer tubing 72 adjacent its distal end 70, the distal lip 82A of proximal component 82 is somewhat flexible and may be resiliently bent outwardly from the distal end 70 so that the distal lip 82A is maintained adjacent the distal end 70 only by the resilient nature of the material, and not by any bonding mechanism.

On the other hand, the distal connector component 84 is secured or bonded to the proximal end 74 of the graft tubing 76, extends circumferentially thereabout, and is relatively rigid. The distal component 84 defines an outwardly and distally sloped lug 84A which cams the distal lip 82A of the proximal component 82 away from the hard polymer tubing end 70 and allows the distal lip 82A to travel over the lug 84A and then resiliently return (or "snap") to its original orientation, with a flange on the distal end of one component (as shown, distal component 82) extending into a recess within the proximal end of the other component (as shown, proximal component 84) to preclude further relative axial motion. In this manner, the distal end 70 of the hard polymer tubing 72 and the proximal end 78 of the graft tubing 76 are secured together by axial movement of components 82, 84 of the snap-fit connector 80, without any relative rotation of the connector components 82, 84 being required.

The connector components 82, 84 are preferably formed of titanium because titanium has acceptable biological properties and either rigidity or high resiliency, depending on its configuration and dimensions.

In a preferred embodiment, the distal connector component 84 additionally defines a proximally projecting lug 84B around which the strain relief material 86 discussed below extends (both inwardly and outwardly thereof), and then the proximal end 74 of the graft tubing 76 extends around the strain relief material 86 about the lug 84B.

In order to protect the graft tubing 76 from the relatively rigid connector 80, preferably a strain-relief material 86 is disposed substantially between the proximal end 74 of the graft tubing 76 and the much harder elements of the connector 80, and in particular the distal connector component 84. Preferably the strain relief material 86 follows the path of the graft tubing 76 to preclude any contact of the distal connector component 84 directly with the graft tubing 76, except possibly beyond distal end 78 of the graft tubing 76. This reduces abrasion of the susceptible graft tubing 76 by the distal connector component 84.

While the graft tubing 76 does come into contact with the hard polymer tubing 72, the resultant abrasion of the graft tubing 76, if any, is much less. Even without the strain relief material 86, there is no contact between the proximal end 74 of the graft tubing 76 and the proximal connector component 82, so it is unnecessary to protect the graft tubing 76 from the proximal connector component 82. Thus, it will be appreciated that the proximal end 74 of the graft tubing 76 is essentially protected from both components 82, 84 of the connector 80.

The strain relief material 86 may simply be a length of hard polymer tubing, similar to tubing 72 but preferably more flexible and elastic. The strain relief material 86 may extend distally of the connector 80 an appreciable length, although such an extension of the strain relief material 86 is not necessary beyond the point required to ensure that there is no contact between the distal connector component 84 and the graft tubing 76.

The inner surface of the graft tubing 76 and the inner surface of the hard polymer tubing 72 are preferably longitudinally aligned so that the relatively smooth transition from one to the other (and in particular, from the hard polymer tubing 72 to the graft tubing 76) does not create a flow-limiting obstruction.

The connector 80 further assists in maintaining patency (the open status) of both the tubings 72, 76.

The present invention further addresses the third problem, namely, the difficulty in securing together the distal end of a tube (for example, a titanium tube entering the heart at a proximal end), and the distal end of a sewable flexible apical cuff (disposed adjacent the proximal end of the inlet cannula 30 to facilitate attachment of the cuff to the heart (e.g., the myocardium) via conventional surgical sewing). The problem here is the complexity and unreliability of the means conventionally used for securing together the apical cuff and the tube.

Figure 6A:
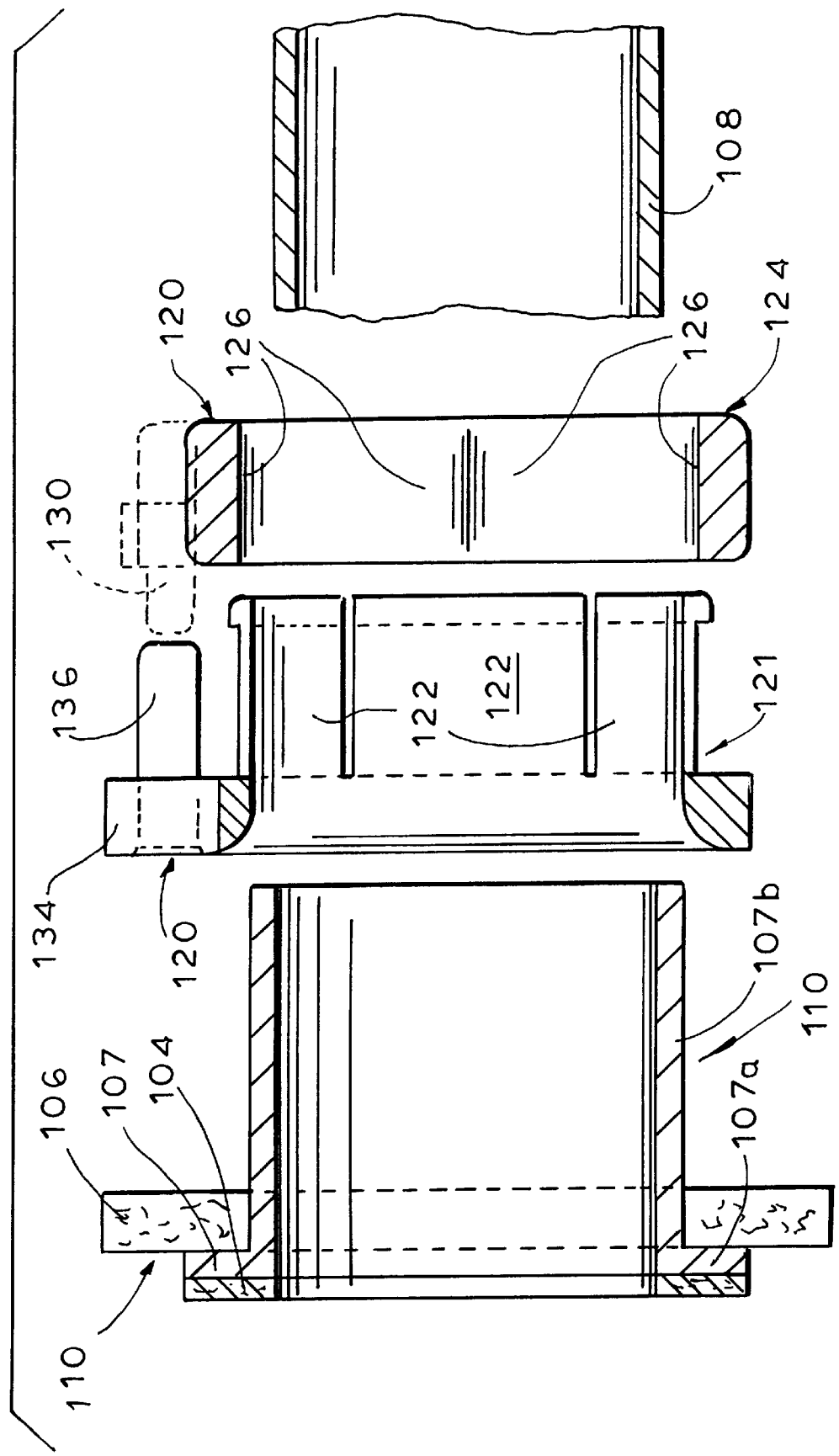
FIG. 6A is an exploded side elevational view thereof, in section.

Referring now to FIGS. 6 and 6A in particular, therein illustrated is a sewable flexible apical cuff, generally designated 110, adapted to be sewn to a heart, e.g., the myocardium (not shown), and a rigid tube 108 adapted to enter the heart chamber (not shown), as well as means, generally designated 120, for securing together the cuff 110 and tube 108. The structural element 107 of the cuff 110 is preferably hat-shaped, with the brim 107*a* of the hat being disposed on the distal end. The brim or distal end 107*a* of the structural element 107 is surrounded on the distal side by a velour ring 104 and on the proximal side by a felt ring 106, and bonded to both rings 104, 106. The velour ring 104 and the felt ring 106 enable ingrowth of the cells of the heart into the velour and felt, thereby to integrate the cuff and the myocardium. The felt ring 106 strengthens the distal surface of the cuff brim 107*a*, provides a means to sew and secure the cuff 110 to the heart, and further protects the cuff brim 107*a* from the securing means 120.

Figure 7:
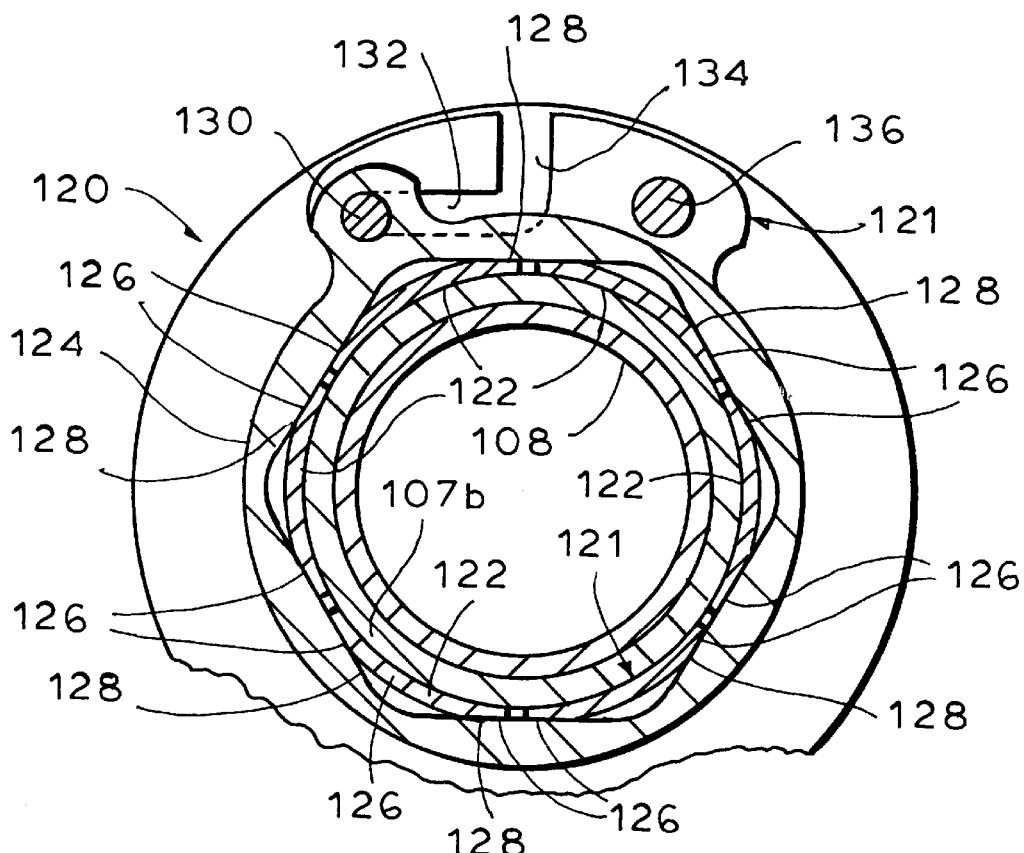
FIG. 7 is a sectional view of the securing means in an open orientation, taken along the line 7—7 of FIG. 6.
Figure 8:
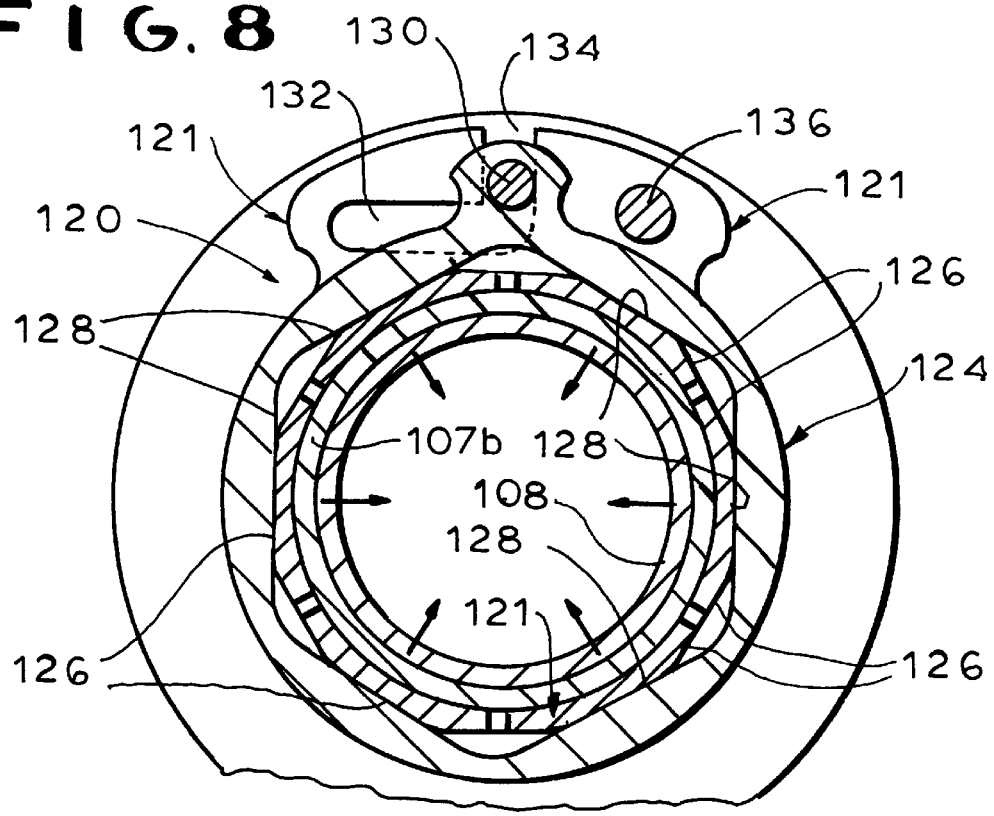
FIG. 8 is a sectional view thereof in a closed orientation, taken along the line 8—8 of FIG. 6.

The securing means 120 includes a collet, generally designated 121, defining multiple radially compressible circumferentially curved fingers 122 (six being shown) and a collar, generally designated 124, for radially inwardly moving (i.e., compressing) the collet fingers 122 to crimp a length 107*b* of the cuff structural element 107 (distal to the cuff brim 107*a* and intermediate the collet 121 and the tube 108) onto the tube 108 as the collar 124 is rotated relative to the collet 121 and its fingers 122 from an initial relative orientation, as illustrated in FIG. 7, to a final relative orientation, as illustrated in FIG. 8.

In the preferred embodiment illustrated in FIGS. 7 and 8, the outer surface of the fingers 122 of resilient plastic collet 121 defines circumferentially spaced flats 126, and the inner surface of the rigid metal collar 124 defines circumferentially spaced flats 128 (e.g., the inner surface of the collar 124 defines a regular polygon (a hexagon being shown)). The fingers 122 and the collar 124 have an initial relative orientation (see FIG. 7) such that the finger flats 126 are radially aligned with the collar flats 128, and a final relative orientation (see FIG. 8) such that the finger flats 126 and the collar flats 128 are not radially aligned, (i.e., are radially offset), so that the inner surface of the collar flats 124 moves the finger flats 126, and hence the fingers 122, radially inwardly towards the tube 108, thereby crimping the distal length of the apical cuff structural element 107 therebetween. In the initial relative orientation, the collar 124 is at least partially rotatable relative to the collet 121 (and in particular the collet fingers 122), and the entire collet 121 is rotatable relative to the tube 108.

As it will be apparent to those skilled in the mechanical arts, alternative collar/collet mechanisms may be used to move the collet fingers inwardly in order to clamp the apical cuff onto the tube. For example, the outer surface of the collet fingers may define outwardly extending lobes, and the inner surface of the collar may define circumferentially spaced recesses for receiving the lobes while the collet and collar are in an initial relative orientation. However, once the collar and collet are moved to the final relative orientation, the portions of the inner surface of the collar intermediate the recesses will press against the finger lobes and thus displace the fingers inwardly toward the tube.

Preferably means are provided to lock the collar 124 in its final relative orientation relative to the collet 121, thereby to preclude release of the apical cuff 110 from the securing means 120 due to accidental rotation of the collar 124 relative to the collet 121. For example, as illustrated, a collar pin 130 may be movable from an initial relative orientation deep within a collet slot 132 into a collet channel 134 when the collet 121 and collar 124 are in the final relative orientation, the slot 132 closing thereafter to prevent accidental return of the collar pin 130 into the slot 132.

Further, the collet 121 may be provided with a pin 136 to facilitate relative movement of the collet 121 and the collar 124 by squeezing together of the two pins 130, 136.

It will be appreciated that the means 120 for securing the cuff and the tube together does not require substantial relative rotation of the tube and the cuff. The required relative rotation of the collar 124 and the collet 121 is relatively minimal, being equal to 180° divided by the number of collet fingers 122 or collar flats 128 (as illustrated, only 30°).

The securing means 120 thus easily and economically secures together the cuff and the tube in a reliable manner.

To summarize, the present invention provides an improved, and preferably implantable, LVAD which is simple and economical to assemble, implant and maintain. The LVAD enables accumulated liquid within the compliance chamber to be withdrawn through a subcutaneous port, thereby increasing the efficiency of the blood pump/compliance chamber subassembly. It may also include an easy-to-operate and reliable means for connecting together the hard polymer tubing and the graft tubing of the outlet cannula without abrasion of the graft tubing by the connector means. It may further include an easy-to-operate and reliable means for securing together the apical cuff and the tube entering the heart chamber.

It will be appreciated that while the invention is described herein primarily in the context of an LVAD, the principles are equally applicable to a right ventricle, left atrium or right atrium assist device.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. In an implantable VAD including a pump, a compliance chamber normally disposed above said pump, and a tube connecting said pump and said compliance chamber in liquid and gaseous communication, the improvement comprising:
(A) said compliance chamber forming:
(i) a reservoir for liquid extending from adjacent the bottom of said compliance chamber upwardly towards the top of said compliance chamber; and
(ii) a chamber for gas disposed above said liquid reservoir and extending upwardly to the top of said compliance chamber, said gas chamber being in gaseous communication with said pump via said tube;
(B) a subcutaneous access port in liquid and gaseous communication with said liquid reservoir for introducing make-up gas into or removing excess gas from said gas chamber via said liquid reservoir and for removing accumulated liquid from said liquid reservoir; and
(C) conduit means connecting said port and said liquid reservoir in liquid and gaseous communication.

2. The VAD of claim 1 wherein said conduit means connects said port and the bottom of said liquid reservoir.

3. The VAD of claim 1 wherein said tube connects said pump and said gas chamber above the top of said liquid reservoir.

4. The VAD of claim 1 additionally including in said compliance chamber a weir having one end passing upwardly through said liquid reservoir and in gaseous communication with said gas chamber, and the other end in gaseous communication with said tube.

5. The VAD of claim 1 wherein the top of said liquid reservoir and the bottom of said gas chamber are the same.

6. In an implantable VAD including an outlet cannula connected to a pump at a proximal end and to a graft tubing adapted to enter the aorta at a distal end;

the improvement wherein:
said outlet cannula comprises a hard polymer tubing commencing adjacent the pump and a relatively soft graft tubing adapted to be secured to the aorta, a distal end of said hard polymer tubing and a proximal end of said graft tubing being secured together by a snap-fit connector.

7. The VAD of claim 6 wherein a strain relief material is disposed substantially between said proximal end of said graft tubing and said snap-fit connector, thereby to protect said graft tubing from said snap-fit connector, maintain said graft tubing patency, and provide a relatively smooth transition from said snap-fit connector to said graft tubing.

8. The VAD of claim 7 wherein said strain relief material is a length of a hard polymer tubing.

9. The VAD of claim 6 wherein said connector is formed of titanium.

10. The VAD of claim 6 wherein said relatively soft graft tubing is formed of segmented polyether urethane urea.

11. In an implantable VAD including a sewable flexible apical cuff adapted to be sewn to a heart and a rigid tube adapted to enter a chamber of the heart, and means for securing together said cuff and said tube, the improvement comprising:
said securing means including a collet defining multiple radially compressible circumferentially curved fingers, and a collar for radially inwardly moving said fingers to crimp a length of said cuff intermediate said collet and said tube onto said tube as said collar is rotated relative to said collet from an initial relative orientation.

12. The VAD of claim 11 wherein the outer surface of said fingers defines circumferentially spaced flats and the inner surface of said collar defines circumferentially spaced flats.

13. The VAD of claim 12 wherein in said initial relative orientation said collar is rotatable relative to said collet.

14. The VAD of claim 13 wherein said fingers and said collar have an initial relative orientation such that said finger flats are radially aligned with, and received in, said collar flats, and a final relative orientation such that said finger flats and said collar flats recesses are radially offset such that said inner surface of said collar compresses said finger flats and hence said fingers inwardly towards said tube, thereby crimping said apical cuff therebetween.

15. The VAD of claim 11 wherein in said initial relative orientation said collet is rotatable relative to said tube.

16. The VAD of claim 11 wherein in said initial relative orientation said collar is rotatable relative to said collet.

17. In an implantable VAD including:
(a) a pump,
(b) a compliance chamber,
(c) a tube connecting said pump and said compliance chamber in liquid and gaseous communication,
(d) an outlet cannula connected to said pump at a proximal end and to graft tubing adapted to enter the aorta at a distal end,
(e) a sewable flexible apical cuff adapted to be sewn to a heart,
(f) a rigid tube adapted to enter a chamber of the heart, and
(g) means for securing together said cuff and said rigid tube,
the improvement comprising:
(A) said compliance chamber forming:
(i) a reservoir for liquid extending from adjacent the bottom of said compliance chamber upwardly towards the top of said compliance chamber; and
(ii) a chamber for gas disposed above said liquid reservoir and extending upwardly to the top of said compliance chamber, said gas chamber being in gaseous communication with said pump via said tube;

(B) a subcutaneous access port in liquid and gaseous communication with said liquid reservoir for introducing make-up gas into or removing excess gas from said gas chamber via said liquid reservoir and for removing accumulated liquid from said liquid reservoir;

(C) conduit means connecting said port and said liquid reservoir in liquid and gaseous communication;

(D) said outlet cannula comprising a hard polymer tubing commencing adjacent the pump and a relatively soft graft tubing adapted to be secured to the aorta, a distal end of said hard polymer tubing and a proximal end of said graft tubing being secured together by a snap-fit connector; and (E) said securing means including a collet defining multiple radially compressible circumferentially curved fingers, and a collar for radially inwardly moving said fingers to crimp a length of said cuff intermediate said collet and said rigid tube onto said rigid tube as said collar is rotated relative to said collet from an initial relative orientation.

* * * * *